US008124808B2

(12) United States Patent
King et al.

(10) Patent No.: US 8,124,808 B2
(45) Date of Patent: Feb. 28, 2012

(54) TRANSALKOXYLATION OF NUCLEOPHILIC COMPOUNDS

(75) Inventors: Stephen W. King, League City, TX (US); William C. Hoffman, Dunbar, WV (US)

(73) Assignee: Union Carbide Chemicals & Plastics Technology LLC, Midland, MI (US)

(*) Notice: Subject to any disclaimer, the term of this patent is extended or adjusted under 35 U.S.C. 154(b) by 283 days.

(21) Appl. No.: 12/587,337

(22) Filed: Oct. 6, 2009

(65) Prior Publication Data

US 2010/0087685 A1 Apr. 8, 2010

Related U.S. Application Data

(60) Provisional application No. 61/195,456, filed on Oct. 6, 2008.

(51) Int. Cl.
C07C 209/22 (2006.01)

(52) U.S. Cl. ......... 564/486; 564/470; 564/479; 564/480

(58) Field of Classification Search .................. None
See application file for complete search history.

(56) References Cited

U.S. PATENT DOCUMENTS

| | | | |
|---|---|---|---|
| 2,861,995 A | 11/1958 | MacKenzie | |
| 3,110,732 A | 11/1963 | Speranza et al. | |
| 3,658,692 A | 4/1972 | Gilbert et al. | |
| 3,847,754 A | 11/1974 | Oliver | |
| 4,073,750 A | 2/1978 | Yates et al. | |
| 4,111,840 A | 9/1978 | Best | |
| 4,123,462 A | 10/1978 | Best | |
| 4,209,424 A | 6/1980 | Le Goff et al. | |
| 4,264,776 A | 4/1981 | Hershman et al. | |
| 4,328,370 A | 5/1982 | Fazio | |
| 4,400,539 A | 8/1983 | Gibson et al. | |
| 4,510,263 A | 4/1985 | Pereira et al. | |
| 4,552,961 A | 11/1985 | Herdle | |
| 4,568,746 A | 2/1986 | Cowherd, III | |
| 4,584,405 A | 4/1986 | Vanderpool | |
| 4,602,091 A | 7/1986 | Brennan | |
| 4,708,945 A | 11/1987 | Murrell et al. | |
| 4,729,981 A | 3/1988 | Kobylinski et al. | |
| 4,801,573 A | 1/1989 | Eri et al. | |
| 4,806,517 A | 2/1989 | Vanderpool et al. | |
| 4,870,044 A | 9/1989 | Kukes et al. | |
| 4,883,826 A | 11/1989 | Marugg et al. | |
| 4,888,316 A | 12/1989 | Gardner et al. | |
| 4,906,782 A | 3/1990 | Hara et al. | |
| 4,922,024 A | 5/1990 | Bowman et al. | |
| 4,927,931 A | 5/1990 | Molzahn et al. | |
| 4,983,735 A | 1/1991 | Hartwell et al. | |
| 5,030,740 A | 7/1991 | Bowman et al. | |
| 5,073,635 A | 12/1991 | Bowman et al. | |
| 5,120,815 A | 6/1992 | Marugg et al. | |
| 5,166,442 A | 11/1992 | Hartwell et al. | |
| 5,225,599 A | 7/1993 | King et al. | |
| 5,225,600 A | 7/1993 | King et al. | |
| 5,248,827 A | 9/1993 | Hara et al. | |
| 5,256,786 A | 10/1993 | Bowman et al. | |
| 5,288,909 A | 2/1994 | Hartwell et al. | |
| 5,321,160 A | 6/1994 | Hironaka et al. | |
| 5,352,835 A | 10/1994 | Dai et al. | |
| 5,410,087 A | 4/1995 | Hartwell et al. | |
| H1447 H | 6/1995 | Linton | |
| 5,455,352 A | 10/1995 | Huellmann et al. | |
| 5,552,363 A | 9/1996 | Pannell et al. | |
| 5,554,793 A | 9/1996 | Hartwell et al. | |
| 5,721,305 A | 2/1998 | Eshuis et al. | |
| 5,750,790 A | 5/1998 | King | |
| 5,851,948 A | 12/1998 | Chuang et al. | |
| 5,935,889 A | 8/1999 | Murrell et al. | |
| 6,117,814 A | 9/2000 | Plecha et al. | |
| 6,124,367 A | 9/2000 | Plecha et al. | |
| 6,169,207 B1 | 1/2001 | Tsuneki et al. | |
| 6,222,008 B1 | 4/2001 | Gelles | |
| 6,235,677 B1 | 5/2001 | Manzer et al. | |
| 6,306,795 B1 | 10/2001 | Ryan et al. | |
| 6,465,530 B2 | 10/2002 | Roy-Auberger et al. | |
| 6,469,214 B2 | 10/2002 | Melder et al. | |
| 6,534,441 B1 | 3/2003 | Bartley et al. | |
| 6,576,796 B1 | 6/2003 | Funke et al. | |
| 6,703,343 B2 | 3/2004 | Park | |
| 6,977,273 B2 | 12/2005 | Roy-Auberger et al. | |
| 7,045,485 B2 | 5/2006 | Kelkar et al. | |

(Continued)

FOREIGN PATENT DOCUMENTS

EP 0075940 4/1983

(Continued)

OTHER PUBLICATIONS

Abstract, Database Beilstein [online], Beilstein Institute for Organic Chemistry, Frankfurt-Main, DE, XP002576591, database accession No. 845679, Jur'Ew Lewi, Doklady Akademii Nauk SSSR, vol. 78, p. 725-727 (1951).

Database Caplus [Online] Chemical Abstracts Service, Columbus, Ohio, US; 2005, Kiebach, Ragnar et al.: "Solvothermal synthesis of [C6H17N3] Sb10516: A new thioantimonate(III) with an in-situ formed organic amine cation," XP002562885 retrieved from STN Database accession No. 2005: 168744 Abstract & Zeitschrift für Naturforschung, B: 2004, 59 (11/12), 1314-1319.

Komiyama et al., "Concentration Profiles in Impregnation of Porous Catalysts: Nickel on Alumina," Journal of Catalysis, vol. 63, School of Chemical Engineering, Cornell University, and Chevron Research Company, pp. 35-52 (1980).

(Continued)

Primary Examiner — Brian J Davis
(74) Attorney, Agent, or Firm — Kagan Binder PLLC (57) ABSTRACT

A method of transalkoxylation of nucleophilic compounds in which an alkoxylated and a nucleophilic compound are combined in a suitable vessel and reacted in the presence of a heterogeneous catalyst under conditions capable of transferring at least one hydroxyalkyl group from the alkoxylated compound to the nucleophilic compound. The method is especially useful in the transalkoxylation of alkanolamines to transfer a hydroxyalkyl group from an alkanolamine having a greater number of hydroxyalkyl groups to an alkanolamine having a lesser number of hydroxyalkyl groups.

19 Claims, 6 Drawing Sheets

U.S. PATENT DOCUMENTS

| | | |
|---|---|---|
| 7,053,246 B2 * | 5/2006 | Gerlach et al. .............. 564/395 |
| 7,053,247 B2 | 5/2006 | Lif et al. |
| 7,056,857 B2 | 6/2006 | Srinivasan et al. |
| 7,067,455 B2 | 6/2006 | Chen et al. |
| 7,256,154 B2 | 8/2007 | Moon et al. |
| 7,323,100 B2 | 1/2008 | Espinoza et al. |
| 7,341,976 B2 | 3/2008 | Espinoza et al. |
| 7,348,293 B2 | 3/2008 | Timken |
| 7,393,978 B2 | 7/2008 | Frauenkron et al. |
| 7,541,310 B2 | 6/2009 | Espinoza et al. |
| 7,595,276 B2 | 9/2009 | Kodama et al. |
| 7,745,369 B2 | 6/2010 | Bhan et al. |
| 7,769,619 B1 | 8/2010 | Krysinski et al. |
| 7,824,656 B2 | 11/2010 | Idem et al. |
| 7,981,836 B2 | 7/2011 | Kanazirev et al. |
| 2003/0013873 A1 | 1/2003 | Neumann et al. |
| 2005/0095189 A1 | 5/2005 | Brey et al. |
| 2006/0030726 A1 | 2/2006 | Telschow |
| 2007/0100144 A1 | 5/2007 | Frauenkron et al. |
| 2008/0003131 A1 | 1/2008 | Bauer et al. |
| 2010/0056366 A1 | 3/2010 | Lee |
| 2010/0087681 A1 | 4/2010 | Petraitis et al. |
| 2010/0087682 A1 | 4/2010 | King et al. |
| 2010/0087683 A1 | 4/2010 | Cook et al. |
| 2010/0087685 A1 | 4/2010 | King et al. |
| 2010/0094007 A1 | 4/2010 | King et al. |
| 2010/0094008 A1 | 4/2010 | King et al. |
| 2010/0137642 A1 | 6/2010 | King et al. |

FOREIGN PATENT DOCUMENTS

| | | |
|---|---|---|
| EP | 0163253 | 12/1985 |
| EP | 0197611 | 10/1986 |
| EP | 0197612 | 10/1986 |
| EP | 0254335 | 1/1988 |
| EP | 0284398 | 9/1988 |
| EP | 0526851 | 2/1993 |
| EP | 0737669 | 10/1996 |
| EP | 1 211 238 A1 | 6/2002 |
| EP | 1211238 | 6/2002 |
| EP | 1249440 | 10/2002 |
| GB | 1508460 | 4/1978 |
| IL | 57019 | 9/1983 |
| RU | 2186761 | 8/2002 |
| RU | 2226188 | 3/2004 |
| RU | 2226189 | 3/2004 |
| WO | WO 99/24389 | 5/1999 |
| WO | 01/44150 A2 | 6/2001 |
| WO | WO 01/66247 | 9/2001 |
| WO | 01/98243 A1 | 12/2001 |
| WO | WO 03/010125 | 2/2003 |
| WO | WO 2005/012223 | 2/2005 |
| WO | WO 2005/014523 | 2/2005 |
| WO | WO 2005/061430 | 7/2005 |
| WO | WO 2006/053342 | 5/2006 |
| WO | WO 2006/060206 | 6/2006 |
| WO | WO 2006/114417 | 11/2006 |
| WO | WO2007/093514 | 8/2007 |
| WO | WO 2008/104582 | 9/2008 |
| WO | WO 2009/083580 | 7/2009 |

OTHER PUBLICATIONS

Reichle, "Reactions of Aliphatic α-ω- Diamines in H+-Pentasils," Journal of Catalysis, vol. 144, Union Carbide Chemicals and Plastics Company, Inc., Specialty Chemicals Division, pp. 556-568 (1993).

Tanabe et al., "A New Hypothesis Regarding the Surface Acidity of Binary Metal Oxides," Bulletin of the Chemical Society of Japan, vol. 47(5), Department of Chemistry, Faculty of Science, Hokkaido University, pp. 1064-1066 (1974).

"Simultaneous manufacture of acyclic and cyclic di- and polyethylenepolyamines," Zagidullun, R.N., USSR., Khimicheskaya Promyshlennost (Moscow, Russian Federation) (1987), (5), 267-9. CODEN: KPRMAW ISSN: 0023-110X. Journal written in Russian. CAN 107:58453, AN 1987: 458453 CAPLUS.

* cited by examiner

FIG. 1. Area percent of products with oxygen concentration.
Reactions were run at 325 °C.

FIG. 2. Area percent of products with gas flow.

Reactions were run at 350 °C and with a 5% $O_2/N_2$ gas feed.

FIG. 3. Area percent of products with various liquid flows.

Reactions were run at 325 °C and with a 5% $O_2/N_2$ gas feed.

FIG. 4. Area percent of products with temperature in °C.
Reactions were run with a 5% O2/N2 gas feed.

FIG. 5. Area percent of products with zirconia catalysts of different surface areas. Reactions were run at 325 °C and with a 5% O2/N2 gas feed.

FIG. 6. Area percent of recycle products at different recycle times.

TRANSALKOXYLATION OF NUCLEOPHILIC COMPOUNDS

PRIORITY

The present non-provisional patent Application claims benefit from U.S. Provisional Patent Application having Ser. No. 61/195,456, filed on Oct. 6, 2008, by Stephen W. King, and titled TRANSALKOXYLATION OF NUCLEOPHILIC COMPOUNDS, wherein the entirety of said provisional patent application is incorporated herein by reference.

FIELD OF THE INVENTION

This invention relates to the transalkoxylation of nucleophilic compounds, especially the transoxylation of compounds having heteroatoms.

BACKGROUND

The preparation of alkoxylated compounds is well known. Typically, the method used to prepare alkoxylated compounds produces a mixture of products that is less than ideal. This is especially in the case in the preparation of alkoxylated, nitrogen compounds such as alkanolamines.

For example, alkanolamines, such as monoethanolamine (MEA), diethanolamine (DEA), and triethanolamine (TEA) are often prepared by reacting ethylene oxide with ammonia. The resulting product is a mixture of MEA, DEA, and TEA. While changing the stoichiometry of the reactants can vary the ratio of these amines in the final product mixture, the reaction is still not sufficiently selective to produce a high level of DEA.

Various approaches have been used to overcome this problem. For example, U.S. Pat. No. 4,264,776 (to Monsanto), Apr. 28, 1981, discloses the catalytic oxidation of tertiary amines with oxygen to form secondary amines in the presence of an active carbon catalyst. An example is provided which treats TEA over active carbon at 115° C. in the presence of oxygen with 60% conversion to DEA.

U.S. Pat. No. 4,328,370 (to TDCC), May 4, 1982, discloses the use of hydrogenation catalysts (Pd, Pt, Rh, Ru) at superatmospheric pressure under anhydrous conditions. For example, TEA is treated with ammonia in the presence of Pd/C or Pd/Al$_2$O$_3$, optionally in the presence of hydrogen, at 200-300° C. to give MEA and DEA.

U.S. Pat. No. 6,469,214 B2 (to BASF) Oct. 22, 2002, discloses the preparation of DEA from a mixture of MEA and TEA in the presence of a strong base and, optionally, ammonia. The preferred strong bases are alkali metal and alkaline earth metal hydroxides, or an alkali metal alkoxide.

WO 2007/093514 A1 (to BASF), Aug. 23, 2007, discloses the conversion of monoethylene glycol into MEA and DEA via a reductive amination.

U.S. Pat. No. 6,169,207 (to Nippon Shokubai Kagaku Kogyo (NSKK)), 2001, discloses selective ethoxylation.

There remains a need for a more efficient method for the preparation of, for example, secondary alkanolamines.

SUMMARY OF THE INVENTION

The present invention provides a method for the transalkoxylation of nucleophilic compounds in which a hydroxyalkyl group on a heteroatom of one compound is transferred to another compound. The method can be practiced with or without the use of additional nucleophiles.

In one embodiment, the present invention provides a method of transferring a hydroxyalkyl group from an alkoxyated compound to a nucleophilic compound comprising the steps of
 a) providing the alkoxylated and nucleophilic compounds;
 b) combining the alkoxylated and nucleophilic compounds in a suitable vessel;
 c) reacting the alkoxylated and nucleophilic compounds in the presence of a heterogeneous catalyst under conditions capable of transferring at least one hydroxyalkyl group from the alkoxylated compound to the nucleophilic compound.

In another embodiment, the present invention provides a method of transalkoxylating an alkoxylated compound comprising the steps of:
 a) providing a first and a second alkoxylated compound;
 b) combining the first and second alkoxylated compounds in a suitable reaction vessel;
 c) reacting the first and second alkoxylated compounds in the presence of a heterogeneous catalyst under conditions capable of transferring at least one hydroxyalkyl group from one of the alkoxylated compounds to the other of the alkoxylated compounds.

In yet another embodiment, the present invention provides a method of transalkoxylating an alkanolamine compound comprising the steps of:
 a) providing a first and a second alkanolamine, each alkanolamine having a different degree of substitution;
 b) combining the first and second alkanolamines in a suitable reaction vessel;
 c) reacting the alkanolamines in the presence of a heterogeneous catalyst under conditions capable of transferring at least one hydroxyalkyl group from one of the alkanolamines to the other of the alkanolamines.

In a further embodiment of the invention, the first and second alkanolamines are selected from (i) a primary and a tertiary alkanolamine, or (ii) a secondary and a tertiary alkanol amine, or (iii) a primary and a secondary alkanolamine.

In the present invention, the transfer of the hydroxyaklyl group is preferably from the compound that has the greater degree of substitution to the compound that has the lesser degree of substitution.

The method of the present invention provides several advantages over the prior art. For example, it eliminates the need to employ strong bases and therefore avoids the problems associated with salt formation during the process. Additionally, it provides a mechanism by which desired alkanolamines, especially DEA, may be produced with high selectivity.

Additionally, the method of the invention is economical in that it can be used with conventional equipment. Furthermore, the present invention employs non-precious metal catalysts, thereby eliminating the need for the use of such materials.

DETAILED DESCRIPTION

The materials required in the process of the invention include an alkoxylated compound, a nucleophile and a heterogeneous catalyst. The alkoxylated compound may be any heteroatom-containing compound in which the heteroatom is substituted with a hydroxyalkyl group. Preferably, the heteroatom is nitrogen (also referred to herein by its chemical symbol "N"). The most preferred alkoxylated compound for use in the present invention is an alkanolamine that may be represented the formula wherein $R^1$ is a hydroxyalkyl group having from 2-20 carbon atoms, and each of $R^2$, and $R^3$ group is independently selected from hydrogen, alkyl groups having from 1 to 20 carbon atoms, and hydroxyalkyl groups having from 2-20 carbon atoms. Preferably, each of $R^1$, $R^2$, and $R^3$ contain from 1-5 carbon atoms, and more preferably from 1-3 carbon atoms. A preferred subclass of alkanolamines for use in the present invention is selected from one or more of MEA, DEA, and TEA.

Any nucleophilic compound may be employed in the process of the present invention. The nucleophilic compound is preferably selected from one or more of an alkanolamine of the formula $(R^1)(R^2)(R^3)N$, wherein $R^1$, $R^2$, and $R^3$ are as defined above in all respects, an alkyleneamine, an alkylamine, water and an alcohol. The alkylene and alkyl groups of the alkyleneamine and alkylamine compounds preferable contain from 1-20 carbon atoms. Preferably, the nucleophilic compound comprises an alkanolamine compound. A preferred subclass of alkanolamines for use as the nucleophilic compound in the present invention is selected from one or more of MEA, DEA, and TEA.

The catalyst used in the present invention may be any heterogeneous catalyst. Preferably the catalyst is not a hydrogenation catalyst. Also the catalyst used in the present invention is preferably not a precious metal catalyst.

A particularly preferred catalyst for use in the present invention is zirconium dioxide ($ZrO_2$), also sometimes referred to as zirconia. Zirconia is a slightly acidic metal oxide compound. Zirconia useful in the present invention may have any surface area. Typically it has a surface area of from about 40-100 m$^2$/g. Preferably the zirconia has a surface area of from about 50-90 m$^2$/g, and more preferably of from about 50-75 m$^2$/g.

The catalyst may also include other materials that enhance the performance of the method of the invention. While the mechanism of the enhancement is not fully understood, it has been found that when certain additives are used in combination with the heterogeneous catalyst the formation of certain impurities is suppressed. These additives include metal oxides that may be oxides of the Group IA, the Group IIA, the Lanthanide series, and the Actinide series of the Periodic Table of the Elements. Preferably the additives are selected from oxides of sodium, potassium, cesium, magnesium, and calcium. The additive generally comprises from about 0.5-15% by weight of the catalyst. Preferably it comprises from about 1-10% by weight, and more preferably from about 1-5% by weight, of the catalyst.

The method of the invention will now be discussed with respect to the transalkoxylation of alkanolamines. Specifically, the method will be discussed with respect to the transethoxylation of MEA by TEA to produce DEA. It is to be understood that this is not intended to limit the present invention, but rather to facilitate the discussion and understanding of the present invention.

The transethoxylation of MEA by TEA to produce DEA may be represented by the general scheme In the process, a feed of an alkoxylated compound (here TEA) and a nucleophilic compound (here MEA) is provided to a suitable reactor. One of the compounds has a higher degree of substitution than the other of the compounds. When the feed comprises two alkanolamines, it preferably comprises one of (i) a primary and a tertiary alkanolamine, (ii) a secondary and a tertiary alkanol amine, or (iii) a primary and a secondary alkanolamine.

Typically, the compounds of the feed are dissolved in a suitable solvent prior to being fed to the reactor. Suitable solvents include ethers, acetonitrile, methanol, ethylene glycol, and water.

The compounds may be dissolved in the solvent at a molar ratio of from about 10:1 to about 1:10 of the alkoxylated compound to the nucleophilic compound, preferably at a ratio of from about 5:1 to about 1:5, and more preferably at a ratio of from about 2:1 to about 1:2. The solution typically comprises from about 1% to about 100% by weight of the reactants. Preferably it comprises from about 5% to about 50% by weight of the reactants. More preferably it comprises from about 10% to about 30% by weight of the reactants.

Once dissolved, the reactants may be fed to a reactor, such as a tubular reactor, and passed over the catalyst. The reaction may be carried out in an inert atmosphere. Alternatively, it may be carried out in an oxygen-containing atmosphere. In either event, the reaction is carried out in an atmosphere that does not adversely affect it. Preferably, the reaction is carried out by simultaneously feeding the dissolved reactants and the gas to the reactor. Suitable gasses include nitrogen alone, or nitrogen with up to 25% by volume of oxygen. Preferably the gas is selected from nitrogen and nitrogen with from about 1-10% (more preferably from 3-5%) by volume oxygen.

The flow rates of the reactants and the gas are adjusted so that the reactants held in the reactor for a time and under conditions capable of transferring at least one hydroxyalkyl group from the more substituted compound to the less substituted compound. While these conditions can be varied to suit the individual reactions, they typically comprise the following:

Hourly Liquid Space Velocity of Reactant Solution (HLSV):

0.3-3.5 hr$^{-1}$, preferably 0.6-2.7 hr$^{-1}$, more preferably 1-2 hr$^{-1}$.

Hourly Gas Space Velocity of Gas (HGSV):

100-600 hr$^{-1}$, preferably 100-500 hr$^{-1}$, more preferably 160-400 hr$^{-1}$.

Reaction Temperature:
200-400° C., preferably 250-380° C., more preferably 300-350° C.

The pressure at which the reaction is carried out is not critical to the invention. It may be carried out under vacuum or at super atmospheric pressure. Preferably it is carried out at atmospheric pressure.

In some embodiments, the most preferable operating conditions are:

| Variable | Conditions |
| --- | --- |
| Gas Feed | 5% $O_2/N_2$ |
| Catalyst | 72 $m^2/g$ $ZrO_2$ |
| HGSV | 200 $hr^{-1}$ |
| HLSV | 1 $hr^{-1}$ |
| Temperature | 325° C. |
| Pressure | Atmospheric |

EXAMPLES

General Procedure. Approximately 3 g of catalyst was charged to a ⅜" O.D. 304 SS tube that was placed in a microfurnace at atmospheric pressure. A 1:1 mol ratio of MEA and TEA was dissolved in water to make a 30 wt % solution and this was fed over the catalyst at the following conditions:

| Temperature | 325° C. |
| --- | --- |
| Pressure | atmospheric |
| Liquid feed | 30 wt % in water |
| Gas feed | 5% $O_2$ in $N_2$ |
| Liquid feed rate | 3 mL/h |
| Gas feed rate | 10 cc/min |

The reaction products were collected neat in a glass container packed with wet ice. The concentration of DEA manufactured was determined using gas chromotography and reported as area percent of product.

Example 1

The above general procedure was followed using medium surface area zirconia (72 $m^2/g$). In one experiment, the gas feed was nitrogen, and in another the gas feed contained 5% oxygen. The results of these reactions are given in Table 1.

TABLE 1

|  | Area % DEA |
| --- | --- |
| $N_2$ | 3-6 |
| 5% $O_2/N_2$ | 13-20 |

Example 2

The general procedure was repeated with the $O_2/N_2$ feed as in Example 1, except that various metal oxide additives were incorporated into the zirconia catalyst (72 $m^2/g$ surface area). These additives reduced the amount of the major by-product, hydroxyethylmorpholine (HEM). With no additive, the DEA/HEM ratio was only 2.3, but 2 wt % Na raised this ratio to 10.6. The results are given in Table 2.

TABLE 2

Effect of Catalyst Additives

|  | Area Percent | | |
| --- | --- | --- | --- |
| Additive | DEA | HEM | DEA/HEM |
| none | 18.5 | 7.9 | 2.3 |
| 5% Ce | 11.3 | 1.7 | 6.6 |
| 7% Y | 21.4 | 4.1 | 5.2 |
| 10% La | 8.7 | 1.5 | 5.9 |
| 2% K | 13.8 | 3.6 | 3.9 |
| 2% Na | 13.0 | 1.2 | 10.6 |
| 4% K | 15.2 | 4.2 | 3.6 |
| 1% Mg | 13.5 | 1.7 | 7.9 |

Example 3

Figure 1:
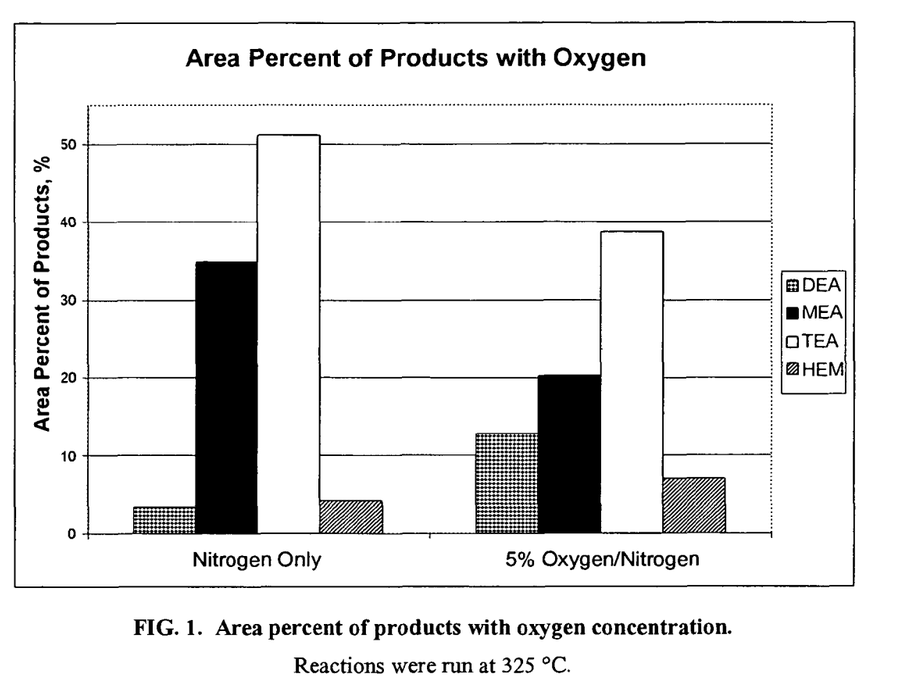
FIG. 1 illustrates the effect of the gaseous atmosphere on the area percentage of products produced.

The general procedure was repeated except that the liquid flow was 6 mL/hr and the gas flow was 13 mL/min. In one experiment the gas feed was nitrogen. In the other experiment the gas feed contained 5% oxygen. The influence of oxygen concentration in the gas feed on the quantity of various reaction products produced is shown in FIG. 1. HEM is the acronym for hydroxyethylmorpholine.

Example 4

Figure 2:
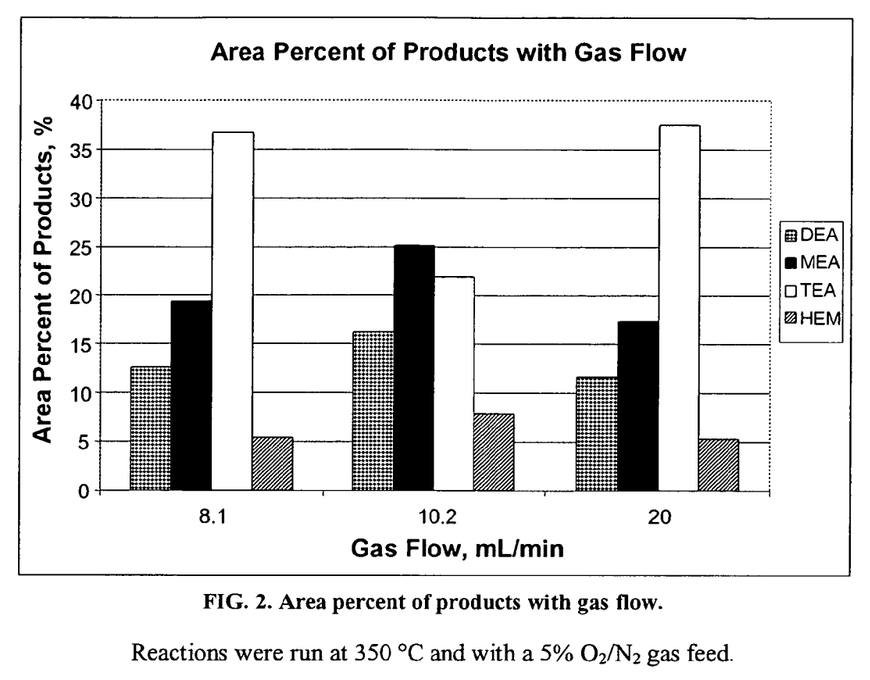
FIG. 2 illustrates the influence of changing the flow rate of the gas feed on the percentage of products produced.

The general procedure was repeated using a 5% $O_2/N$ gas feed except that the gas flow rate was varied and the reaction was run at 350° C. The influence of gas flow rate on the quantity of the reaction products produced is shown in FIG. 2.

Example 5

Figure 3:
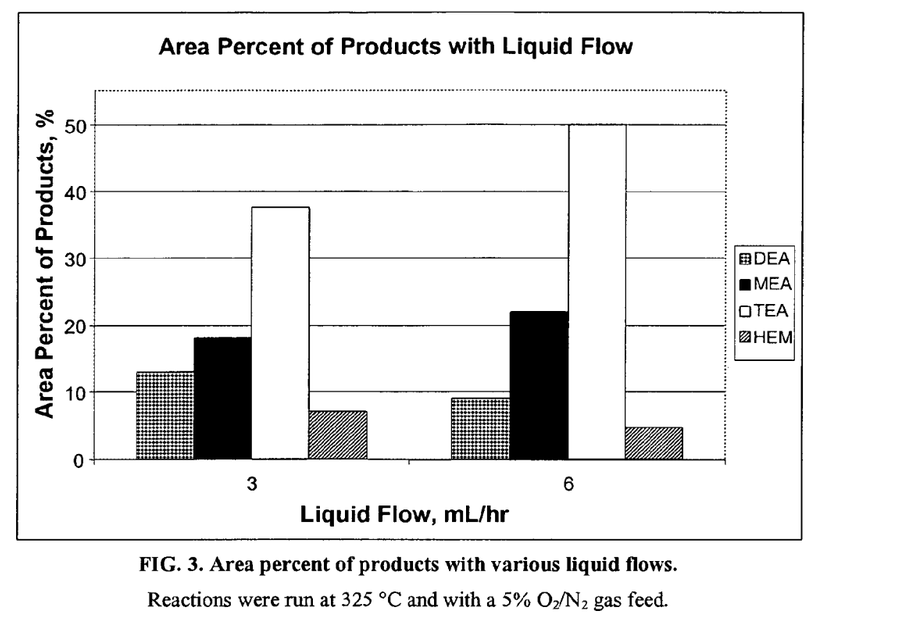
FIG. 3 illustrates the influence of changing the flow rate of the liquid feed on the area percentage of products produced using different liquid feed rates.

The general procedure was repeated except that the liquid flow rate was varied. The influence of liquid feed rate on the quantity of the reaction products produced is shown in FIG. 3.

Example 6

Figure 4:
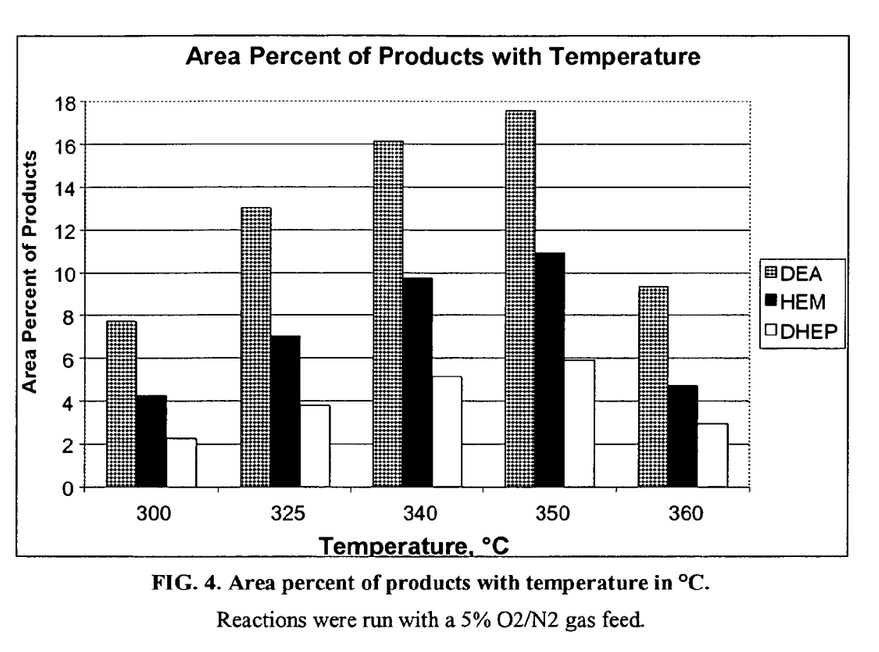
FIG. 4. illustrates the influence of reaction temperature on the percentage of products produced.

The general procedure was repeated except that the reaction temperature was started at 300° C. and increased to 360° C. slowly. The influence of reaction temperature on the quantity of the products produced is shown in FIG. 4.

Example 7

Figure 5:
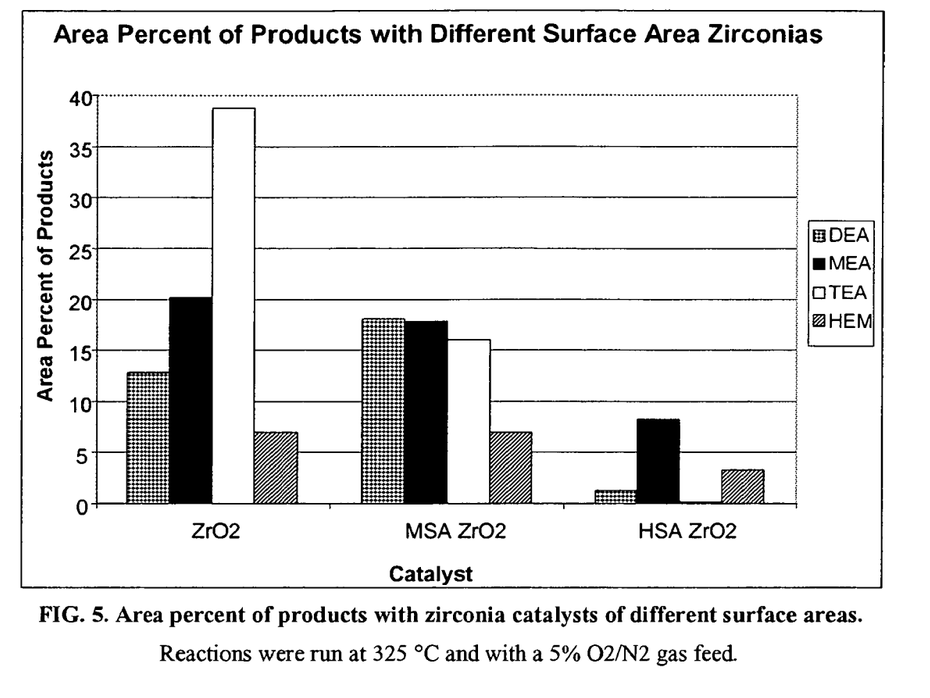
FIG. 5. illustrates the influence of the catalyst surface area on the area percentage of products produced.

The general procedure was repeated except that zirconia having three different surface areas were used: high (HSA 98 $m^2/g$), medium (MSA 72 $m^2/g$), and typical surface area ($ZrO_2$ 52 $m^2/g$). The influence of the surface area of zirconia catalyst on the quantity of the products produced is shown in FIG. 5.

Example 8

Figure 6:
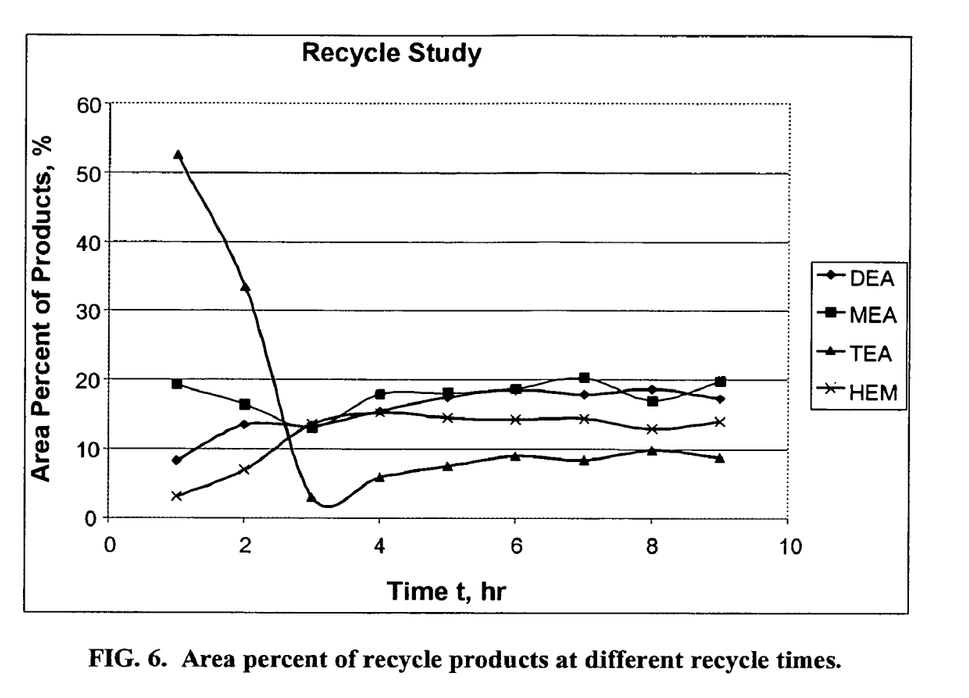
FIG. 6. illustrates the influence of recycle on the quantity of product produced over time.

A recycle experiment was performed. The feed contained, in area percent, 15.6% MEA, 33.1% TEA, 13.1% DEA, 7.1% HEM, and 4.4% dihydroxyethylpiperazine (DHEP). The recycle feed was charged to the tubular reactor and reacted under the operating conditions of Example 1 except that the residence time was varied. The influence of recycle on the quantity of products produced is shown in FIG. 6. As shown, the amount of DEA increased over time.

Example 9

The general procedure of Example 2 was followed except that a 15 wt % aqueous TEA solution was fed at 15 mL/h. The catalyst was a medium surface area zirconia with 10 wt % $CeO_2$. The results are shown in Table 3.

TABLE 3

Results of 15% aqueous TEA Feed

| | GC Area % |
|---|---|
| TEA | 61 |
| DEA | 26 |
| EG | 1.6 |
| HEM | 3.8 |

What is claimed is:

1. A method of transferring a hydroxyalkyl group from an alkoxylated compound to a nucleophilic compound comprising the steps of:
   a) providing the alkoxylated and nucleophilic compounds, wherein the alkoxylated compound has the formula $(R^1)(R^2)(R^3)N$ wherein $R^1$ is a hydroxyalkyl group having from 2-20 carbon atoms, and each $R^2$, and $R^3$ group is independently selected from hydrogen, alkyl groups having from 1 to 20 carbon atoms, and hydroxyalkyl groups having from 2-20 carbon atoms, and wherein the nucleophilic compounds is selected from $(R^1)(R^2)(R^3)N$, wherein $R^1$, $R^2$, and $R^3$ are as defined above in all respects, an alkyleneamine, an alkylamine, water and an alcohol;
   b) combining the alkoxylated and nucleophilic compounds in a suitable vessel;
   c) reacting the alkoxylated and nucleophilic compounds in the presence of a zirconia-containing heterogeneous catalyst under conditions capable of transferring at least one hydroxyalkyl group from the alkoxylated compound to the nucleophilic compound.

2. The method of claim 1, wherein the nucleophilic compound is selected from an alkanolamine, an alkyleneamine, an alkylamine, ammonia, water, and an alcohol.

3. The method of claim 1, wherein the alkoxylated compound is an alkanolamine that has a different degree of substitution than the alkanolamine of the nucleophilic compound.

4. The method of claim 3, wherein the nucleophilic compound is an alkanolamine.

5. The method of claim 1, wherein the heterogeneous catalyst is a non-hydrogenation catalyst.

6. The method of claim 1, wherein the heterogeneous catalyst is a non-precious metal catalyst.

7. The method of claim 1, wherein the zirconia-containing catalyst has a surface area of from about 40 to 100 m²/g.

8. The method of claim 1, wherein the catalyst further comprises a metal oxide additive.

9. The method of claim 8, wherein the metal oxide is selected from oxides of the Group IA, Group IIA, Lanthanide, and Actinide series of elements in the Periodic Table of the Elements.

10. The method of claim 9, wherein the metal oxide is selected from oxides of sodium, potassium, cesium, magnesium, and calcium.

11. The method of claim 1, wherein the zirconia-containing heterogeneous catalyst further comprises an additive that comprises from 0.5 to 15% by weight of the zirconia.

12. The method of claim 1, wherein the reaction takes place in water.

13. The method of claim 1, wherein the reaction occurs in an inert atmosphere.

14. The method of claim 1, wherein the reaction takes place in a nitrogen-containing atmosphere.

15. The method of claim 14, wherein the nitrogen-containing atmosphere further comprises up to 25% by volume oxygen.

16. The method of claim 1, wherein the reaction occurs at a temperature in the range of from 200° C. to 400° C.

17. A method of transalkoxylating an alkoxylated compound comprising the steps of:
   a) providing a first and a second alkoxylated compound, wherein the first and second alkoxylated compounds have the formula $(R^1)(R^2)(R^3)N$ wherein $R^1$ is a hydroxyalkyl group having from 2-20 carbon atoms, and each $R^2$, and $R^3$ group is independently selected from hydrogen, alkyl groups having from 1 to 20 carbon atoms, and hydroxyalkyl groups having from 2-20 carbon atoms;
   b) combining the first and second alkoxylated compounds in a suitable reaction vessel;
   c) reacting the first and second alkoxylated compounds in the presence of a zirconia-containing heterogeneous catalyst under conditions capable of transferring at least one hydroxyalkyl group from one of the alkoxylated compounds to the other of the alkoxylated compounds.

18. The method of claim 17, wherein the first and second alkanol amines each have a different degree of substitution.

19. The method of claim 18, wherein the first and the second alkanolamine is selected from (i) a primary and a tertiary alkanolamine, or (ii) a secondary and tertiary alkanolamine, or (iii) a primary and a secondary alkanol amine.

* * * * *